United States Patent [19]

Roberts

[11] Patent Number: 4,939,302

[45] Date of Patent: Jul. 3, 1990

[54] PROCESS FOR PREPARING STABLE ORGANIC HYDROXYSULFIDE COMPOSITIONS

[75] Inventor: John S. Roberts, Bartlesville, Okla.

[73] Assignee: Phillips Petroleum Company, Bartlesville, Okla.

[21] Appl. No.: 227,338

[22] Filed: Aug. 2, 1988

[51] Int. Cl.$^5$ .......................................... C07C 148/00
[52] U.S. Cl. ...................................................... 568/55
[58] Field of Search .......................................... 568/55

[56] References Cited

U.S. PATENT DOCUMENTS

| | | | |
|---|---|---|---|
| 2,703,784 | 3/1955 | Fields | 252/32.7 E |
| 3,567,782 | 3/1971 | Warner et al. | 568/55 |
| 3,775,483 | 11/1973 | Frederickson et al. | 568/55 |
| 3,834,902 | 9/1974 | Wright | 430/89 |
| 4,310,706 | 1/1982 | Strege | 568/55 |
| 4,735,980 | 4/1988 | Sturm et al. | 524/392 |

OTHER PUBLICATIONS

E. Larribau et al., Chem. Abstracts, vol. 93: 51415s (1980).
Organic Chemistry of Bivalent Sulfur, vol. II, pp. 205, 206, E. Emmet Reid (1960).
Chemical Abstract, 48,11485 (Ger. 869,064).
Chemical Abstract, 27, 268 (1933).
Chemical Abstract, 90, 188322v (1979).

Primary Examiner—Mary E. Ceperley
Attorney, Agent, or Firm—Laney, Dougherty, Hessin & Beavers

[57] ABSTRACT

An improved process is provided for reacting starting materials in the presence of an acid catalyst in a reaction zone to produce an acid sensitive product. The starting materials are circulated in the reaction zone through a fixed bed of solid acid-type ion exchange resin to thereby catalyze the reaction, and the resulting reaction product is withdrawn from the reaction zone. Starting materials comprised a mercaptan and an aldehyde or ketone are reacted in accordance with the process to produce high yields of aliphatic hydroxyalkyl or hydroxyaryl sulfide.

17 Claims, 1 Drawing Sheet

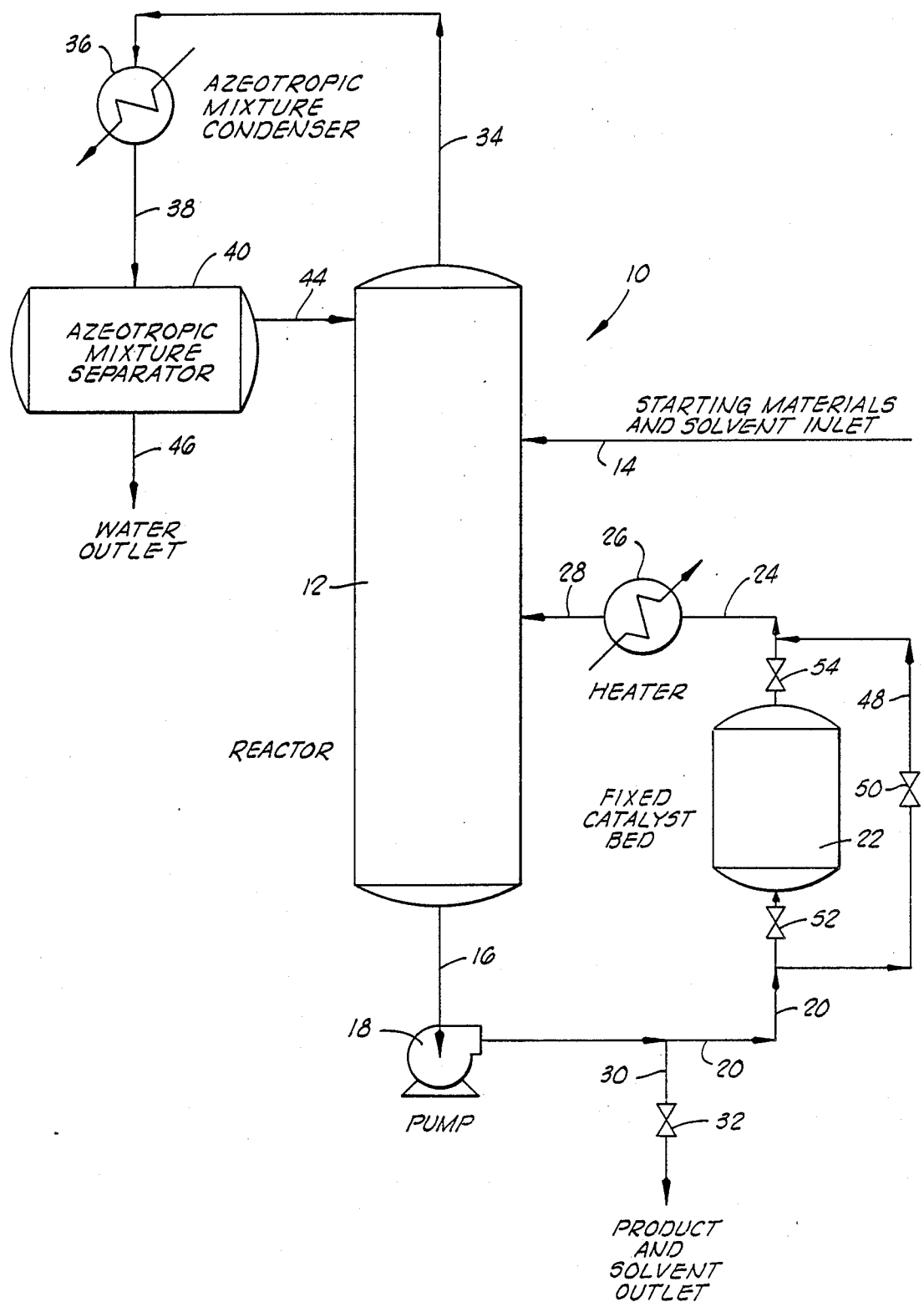

PROCESS FOR PREPARING STABLE ORGANIC HYDROXYSULFIDE COMPOSITIONS

BACKGROUND OF THE INVENTION

1. Field of the Invention

The present invention relates generally to organic hydroxysulfide compositions and an improved process for preparing such compositions.

2. Description of the Prior Art

The acid catalyzed reaction of formaldehyde with mercaptans (aliphatic thiols) to produce aliphatic hydroxymethyl sulfide compositions has been known heretofore. However, the hydroxymethylated compositions produced have been unstable and are sensitive to acid. In general, when starting materials are reacted in the presence of an acid catalyst to produce acid sensitive products such as aliphatic alphahydroxyalkyl or hydroxyaryl sulfides, the products are subject to degradation as a result of prolonged contact with the acid catalyst, and problems in separating the acid catalyst from the product are often encountered, all of which results in low yields. Thus, there is a need for an improved process for preparing an acid sensitive product by reacting starting materials in the presence of an acid catalyst.

By the present invention such an improved process for producing acid catalyzed products which are acid sensitive is provided whereby high product yields can be obtained. Further, an improved process for reacting mercaptans with aldehydes or ketones in the presence of an acid catalyst to produce stable aliphatic hydroxyalkyl or hydroxyaryl sulfides is provided. Also, the present invention provides a novel and stable dodecyl hydroxymethyl sulfide composition.

SUMMARY OF THE INVENTION

A process for reacting starting materials in the presence of an acid catalyst in a reaction zone to produce an acid sensitive product is provided. The process comprises circulating the starting materials in the reaction zone through a fixed bed of solid acid-type ion exchange resin to thereby catalyze the reaction and then withdrawing the resultant reaction product from the reaction zone.

In another aspect, an improved process for producing aliphatic hydroxyalkyl or hydroxyaryl sulfides is provided. The process comprises the steps of charging starting materials to a reaction zone comprised of a mercaptan and an aldehyde or ketone, circulating the resultant mixture of the starting materials in the reaction zone through a fixed bed of solid acid-type ion exchange resin catalyst whereby the mixture catalytically reacts to form an aliphatic hydroxyalkyl or hydroxyaryl sulfide composition and withdrawing the produced composition from the reaction zone.

When the aldehyde or ketone starting material is dissolved in water, the process includes the additional steps of combining a solvent for the produced composition with the starting materials which forms an azeotropic mixture with water, heating the resulting starting material mixture during the reaction to vaporize the azeotropic mixture formed by the water and the solvent, withdrawing the vaporized azeotropic mixture from the reaction zone, condensing the vaporized azeotropic mixture, separating the condensed azeotropic mixture into condensed water and condensed solvent components, withdrawing the condensed water component and returning the condensed solvent component to the reaction zone. The produced aliphatic hydroxyalkyl or hydroxyaryl sulfide composition and solvent are withdrawn from the reaction zone and separated whereby the composition is recovered.

In yet another aspect of the present invention, a novel dodecyl hydroxymethyl sulfide composition $(CH_3(CH_2)_{11}SCH_2OH)$ is provided.

It is, therefore, a general object of the present invention to provide an improved process for reacting starting materials in the presence of an acid catalyst to produce an acid sensitive product.

A further object of the present invention is the provision of a process for producing organic hydroxysulfide compositions, and particularly, aliphatic hydroxyalkyl or hydroxyaryl sulfide compositions.

Other objects, features and advantages of the present invention will be readily apparent to those skilled in the art upon a reading of the description of preferred embodiments which follows when taken in conjunction with the accompanying drawing.

DESCRIPTION OF THE DRAWING

In the accompanying drawing forming a part of this disclosure, a system of apparatus which can be utilized for carrying out the improved process of the present invention is illustrated schematically.

DESCRIPTION OF PREFERRED EMBODIMENTS

In accordance with the present invention an improved process for reacting starting materials in the presence of an acid catalyst to produce an acid sensitive product is provided. The starting materials are charged to a reaction zone and are circulated within the reaction zone through a fixed bed of solid acid-type ion exchange resin catalyst. The acid-type ion exchange resin catalyzes the reaction between the starting materials to produce the desired acid sensitive product, and the product is withdrawn from the reaction zone and from the acid-type ion exchange resin catalyst prior to when degradation of the product occurs. By carefully controlling the contact of the acid sensitive product with the acid catalyst and avoiding catalyst-product separation problems, high yields of product are realized.

In a more specific aspect of the present invention, an improved process for producing aliphatic hydroxyalkyl or hydroxyaryl sulfides is provided. In accordance with the process, starting materials comprised of a mercaptan and an aldehyde or ketone are charged to a reaction zone. While within the reaction zone, the starting materials are circulated through a fixed bed of solid acid-type ion exchange resin catalyst for a time sufficient for the starting materials to react and form an aliphatic hydroxyalkyl or hydroxyaryl sulfide composition. When the reaction has gone to completion and before the acid sensitive product composition is degraded by contact with the acid catalyst, the product composition is withdrawn from the reaction zone.

When the aldehyde or ketone utilized is dissolved in an aqueous solvent, e.g., an aqueous formaldehyde solution, the process includes the additional steps of combining a solvent for the produced composition with the starting materials which forms an azeotropic mixture with the water. The starting materials are heated during the reaction whereby the water-solvent azeotropic mixture is vaporized. The vaporized azeotropic mixture is withdrawn from the reaction zone, condensed and separated into water and solvent components. The condensed water is withdrawn and the solvent is recycled to the reaction zone. The product composition and solvent are then withdrawn from the reaction zone and separated whereby the product composition is recovered.

A variety of commercially available solid acid-type ion exchange resins are suitable for use in accordance with the improved process of the present invention. For example, solid acid-type ion exchange resins are manufactured by the Rohm & Haas Company of Philadelphia, Pa. under the trade designations "Amberlyst 15" and "Amberlyst XN-1010". Amberlyst 15 and Amberlyst XN-1010 are both styrene divinyl benzene resins which have been modified by addition of a reactive acid functionality. Both are strongly acidic macro-reticular cation exchange resins Amberlyst 15 has less surface area but a higher ion exchange capacity than Amberlyst XN-1010. Examples of other suitable resins which can be used are those marketed by the Rohm & Haas Company under the trade designation "Amberlite" including Amberlite 200, Amberlite 252 and others. The Amberlite resins are also acidic styrene divinyl benzene resins, but they require pretreatment with a strong acid while the Amberlyst resins do not.

Of the various solid acid-type ion exchange resins which can be utilized, the strongly acidic macro-reticular cation exchange resins which do not require acid pretreatment are the most preferred.

In the process of this invention for producing aliphatic hydroxyalkyl or hydroxyaryl sulfides from mercaptan and aldehyde or ketone starting materials, various mercaptans (also known as aliphatic thiols) can be used. Alkyl mercaptans are presently commercially available which are prepared in various ways including reacting hydrogen sulfide with olefins, alkyl halides and aklylene epoxides. Examples of suitable alkyl mercaptans useful in accordance with this invention are n-decyl mercaptan, n-dodecyl mercaptan, secondary and tertiary dodecyl mercaptan, n-tetradecyl mercaptan, tertiary tetradecyl mercaptan, and various isomers of dodecyl and tetradecyl mercaptan. Generally, alkyl mercaptans having from 10 to 24 carbon atoms are preferred.

The aldehydes or ketones useful in accordance with the present invention are those represented by the formula:

wherein R and $R^1$ are each independently hydrogen or an alkyl or aryl group having from about 1 to about 24 carbon atoms. Examples of aldehydes falling within the above definition are formaldehyde, acetaldehyde, decanal and octadecanal. Examples of ketones are dimethyl ketone methylethyl ketone, dibutyl ketone and n-octadecyl methyl ketone.

When a mercaptan is reacted with an aldehyde or ketone as described above in the presence of an acid catalyst, an aliphatic hydroxyalkyl or hydroxyaryl sulfide composition is produced represented by the formula:

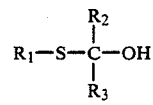

wherein $R_1$ is an aliphatic group and $R_2$ and $R_3$ are each independently hydrogen or an alkyl or aryl group having from about 1 to about 24 carbon atoms.

The process for carrying out the above described reaction in accordance with the present invention comprises the steps of charging the mercaptan and aldehyde or ketone starting materials to a reaction zone, circulating the resultant mixture of starting materials in the reaction zone through a fixed bed of solid acid-type ion exchange resin catalyst whereby the mixture catalytically reacts to form the aliphatic hydroxyalkyl or hydroxyaryl sulfide composition, and then withdrawing the composition from the reaction zone.

A novel stable composition which can be produced utilizing the improved process of the present invention is dodecyl hydroxymethyl sulfide, i.e., $CH_3(CH_2)_{11}SCH_2OH$. Such composition is useful as a lubrication additive and as an intermediate in the production of other lubrication additives and pesticides.

In producing dodecyl hydroxymethyl sulfide, n-dodecyl mercaptan, an aqueous formaldehyde solution and a hexane solvent are charged to a reaction zone. While within the reaction zone, the mixture of starting materials is heated to vaporize the azeotropic mixture formed by the water in the aqueous formaldehyde solution and the hexane solvent. The mixture is circulated while being heated in the reaction zone through a fixed bed of solid acid-type ion exchange resin catalyst for a period of time sufficient for the starting materials to catalytically react to completion whereby a high yield of dodecyl hydroxymethyl sulfide is produced. During the reaction, the vaporized azeotropic mixture is withdrawn from the reaction zone, condensed and separated into condensed water and hexane components. The condensed water is withdrawn, and the condensed hexane is returned to the reaction zone. The product composition, dodecyl hydroxymethyl sulfide, and hexane solvent are withdrawn from the reaction zone and separated to recover stable dodecyl hydroxymethyl sulfide. The separation of the product composition from the hexane solvent is conveniently carried out by vacuum evaporation of the hexane.

As will be understood by those skilled in the art, when the aldehyde or ketone starting material is utilized in the form of an aqueous solution, solvents other than hexane can be utilized which form azeotropic mixtures with water and which dissolve the product sulfide composition. Preferred such solvents are those that vaporize at temperatures below about 100° C. at atmospheric pressure, e.g., propane, butane, pentane, isobutane, cyclohexane and benzene.

Referring now to the drawing, a system of apparatus which can be utilized for carrying out the improved process of the present invention is illustrated and generally designated by the numeral 10. Included in the system 10 is a reactor 12 to which the starting materials including water and azeotropic mixture forming solvent are charged by means of a conduit 14 connected thereto. A conduit 16 is connected between an outlet at the bottom of the reactor 12 and a pump 18. The discharge of the pump 18 is connected by a conduit 20 to the inlet of a vessel 22 containing a fixed bed of acid-type ion exchange resin catalyst. The outlet of the vessel 22 is connected by a conduit 24 to the inlet of a heater 26. A conduit 48 for bypassing the vessel 22 is connected to the conduits 20 and 24, and shutoff valves 52, 54 and 50 are disposed in the conduits 20, 24 and 48, respectively. A conduit 28 connected to the outlet of the heater 26 is connected to an inlet connection in the reactor 12. A conduit 30 having a shutoff valve 32 disposed therein is connected to the conduit 20 for withdrawing reaction product and solvent from the system 10.

A vapor outlet at the top of the reactor 12 for withdrawing vaporized azeotropic mixture therefrom is connected by a conduit 34 to the inlet of an azeotropic mixture condenser 36. The outlet of the condenser 36 is connected by a conduit 38 to the inlet of a separator 40. The separator 40 functions to separate the condensed azeotropic mixture into condensed water and solvent components. The solvent component is withdrawn from an outlet in the separator 40 and returned to the reactor 12 by a conduit 42 connected therebetween, and the separated water component is withdrawn from the separator 40 by way of an outlet therein and a conduit 46 connected thereto.

In operation of the system 10, starting materials such as n-dodecyl mercaptan, an aqueous formaldehyde solution and hexane are conducted to the reactor 12 by the conduit 14. The starting material mixture is withdrawn from the bottom of the reactor 12 by way of the conduit 16 and pumped by the pump 18 through the vessel 22 containing the fixed catalyst bed by way of the conduit 20 and the open shutoff valve 52 therein, through the heater 26 by way of the conduit 24 and open shutoff valve 54 therein and back to the reactor 12 by way of the conduit 28. As the starting materials are circulated by the pump 18, they are contacted by the acid-type ion exchange resin catalyst within the vessel 22 so that they react, and they are heated in the heater 26 whereby the azeotropic mixture formed by the water from the aqueous formaldehyde solution and the hexane solvent is continuously vaporized. The vaporized azeotropic mixture is withdrawn from the reactor 12 by way of the conduit 34 and condensed by the condenser 36. The condensed azeotropic mixture enters the separator 40 by way of the conduit 38 and is separated into condensed water and condensed hexane components. The water is removed from the bottom of the separator 40 by way of the conduit 46 and the hexane is returned to the reactor 12 by way of the conduit 44.

Thus, as the mixture of starting materials is circulated through the vessel 22 containing the fixed resin catalyst bed and through the heater 26, the starting materials are caused to react and the azeotropic mixture of water and solvent is vaporized so that water is removed from the mixture. The circulation is continued until the reaction has gone to completion at which time if the water has not all been removed, the bypass shutoff valve 50 is opened and the shutoff valves 52 and 54 are closed so that the vessel 22 and acid-type ion exchange resin therein are bypassed and the product composition formed does not continue to contact the catalyst and degrade. Once all of the water has been removed from the mixture containing the product composition, the valve 32 is opened and the product composition dissolved in the solvent is removed from the system 10. The product composition can then be isolated from the solvent, if desired, e.g., by vacuum evaporation of the solvent.

In order to further illustrate the present invention, the following examples are given.

EXAMPLE 1

162.2 grams of a 37% by weight aqueous solution of formaldehyde (equivalent to 2 moles) and 404 grams of n-dodecyl mercaptan (equivalent to 2 moles) were placed in a reaction pot along with 2 grams of Amberlyst 15 acid-type ion exchange resin catalyst. The reactants and catalyst were heated to 100° C. and allowed to react for 2 hours. Thereafter, the catalyst was removed from the reaction product by filtration. The product composition was identified to be dodecyl hydroxymethyl sulfide by gas chromatography, IR, NMR and elemental analysis, and a yield of only 58.3% was realized.

EXAMPLE 2

162.2 grams of a 37% by weight aqueous solution of formaldehyde (equivalent to 2 moles), 404 grams of n-dodecyl mercaptan (equivalent to 2 moles) and 250 milliliters of hexane were placed in a one liter flask equipped with an overhead azeotropic mixture condenser and a condensed water and hexane component separator. A fixed bed of Amberlyst 15 acid-type ion exchange resin catalyst was provided, and the reaction mixture in the flask was circulated by a pump from the flask through the catalyst bed and back to the flask at a rate of about 2 milliliters per minute for a time period of 4 hours. While the reaction mixture was being circulated through the catalyst bed, it was heated to a temperature of approximately 100° C. whereby the azeotropic mixture formed by the hexane and water in the flask was vaporized, withdrawn from the flask and condensed. The water component of the condensed azeotropic mixture was separated from the hexane component and withdrawn, and the hexane was returned to the reaction flask. A 91.8% yield of dodecyl hydroxymethyl sulfide was realized after the hexane was removed by vacuum evaporation.

Thus, the present invention is well adapted to attain the ends and advantages mentioned as well as those inherent therein. While numerous changes in the arrangement and condition of process steps may suggest themselves to those skilled in the art, such changes are encompassed within the spirit of the invention as defined by the appended claims.

What is claimed is:

1. In a process for reacting a mercaptan with a second reactant selected from the group consisting of aldehydes and ketones in the presence of an acid catalyst in a reaction zone to produce an acid sensitive aliphatic hydroxyalkyl or hydroxyaryl sulfide product, the improvement comprising:

collecting said mercaptan, said second reactant and sulfide product produced therefrom in a first section of said reaction zone, said reaction zone also having a second section with a fixed bed of solid acid-type ion exchange resin catalyst disposed therein;

circulating the resultant mixture collected in said first section through said second section so that said mercaptan and said second reactant catalytically react to form said sulfide product; and then withdrawing the resultant reaction product from said reaction zone.

2. The process of claim 1 wherein said solid acid type ion exchange resin is selected from the group consisting of strongly acidic macro-reticular cation exchange resins.

3. The process of claim 2 wherein said mercaptan is an alkyl mercaptan having from 10 to 24 carbon atoms.

4. The process of claim 3 wherein said aldehydes and ketones are represented by the formula:

$$R-\overset{O}{\underset{\|}{C}}-R^1$$

wherein R and $R^1$ are each independently hydrogen or an alkyl or aryl group having from about 1 to about 24 carbon atoms.

5. The process of claim 3 wherein said alkyl mercaptan is n-dodecyl mercaptan, said second reactant is formaldehyde and said acid sensitive product is dodecyl hydroxymethyl sulfide.

6. The process of claim 5 wherein said catalyst is a styrene divinyl benzene resin having acid functionality.

7. The process of claim 2 wherein said second reactant is dissolved in an aqueous solvent.

8. The process of claim 7 which is further characterized to include the steps of:
combining a solvent for said sulfide product with said mercaptan and said second reactant, said solvent forming an azeotropic mixture with water present in said reaction zone;
heating the contents of said reaction zone during said reaction to vaporize said azeotropic mixture;
withdrawing said vaporized azeotropic mixture from said reaction zone during said reaction;
condensing said vaporized azeotropic mixture; separating the condensed azeotropic mixture into condensed water and condensed solvent components;
withdrawing said condensed water component; and
returning said condensed solvent component to said reaction zone.

9. The process of claim 8 wherein said solvent which forms an azeotropic mixture with water is hexane.

10. A process for producing a hydrosulfide compound having the formula:

$$R_1-S-\underset{R_3}{\overset{R_2}{\underset{|}{C}}}-OH$$

wherein $R_1$ is an alkyl group from 10 to 24 carbon atoms, and $R_2$ and $R_3$ are each independently hydrogen or an alkyl or aryl group having from about 1 to about 24 carbon atoms comprising the steps of:
charging starting materials to a reaction zone comprised of an alkyl mercaptan having from 10 to 24 carbon atoms and a second reactant having the formula:

$$R-\overset{O}{\underset{\|}{C}}-R^1$$

wherein R and $R^1$ are each independently hydrogen or an alkyl or aryl group having from about 1 to about 24 carbon atoms;
collecting said starting materials and hydroxysulfide compound produced therefrom in a first section of said reaction zone, said reaction zone also having a second section with a fixed bed of solid acid-type ion exchange resin catalyst disposed therein;
circulating the resultant mixture collected in said first section through said second section whereby said mercaptan and said second reactant catalytically react to form said hydroxysulfide compound; and
withdrawing said hydroxysulfide compound from said reaction zone.

11. The process of claim 10 wherein said solid acid-type ion exchange resin is selected from the group consisting of strongly acidic macro-reticular cation exchange resins.

12. The process of claim 11 wherein $R_1$ is a dodecyl group and $R_2$, $R_3$, R and $R^1$ are each hydrogen.

13. The process of claim 10 wherein said second reactant is dissolved in water and wherein said process is further characterized to include the steps of:
combining a solvent for said produced hydroxysulfide compound with said starting materials which forms an azeotropic mixture with said water;
heating the contents of said reaction zone during said reaction to vaporize the azeotropic mixture formed by said water and said solvent;
withdrawing said vaporized azeotropic mixture from said reaction zone during said reaction;
condensing said vaporized azeotropic mixture;
separating the condensed azeotropic mixture into condensed water and condensed solvent components;
withdrawing said condensed water component; and
returning said condensed solvent component to said reaction zone.

14. A process for producing dodecyl hydroxymethyl sulfide comprising:
charging starting material to a reaction zone comprised of n-dodecyl mercaptan, an aqueous formaldehyde solution and a hexane solvent;
collecting said starting materials and dodecyl hydroxymethyl sulfide produced therefrom in a first section of said reaction zone, said reaction zone also having a second section with a fixed bed of solid acid-type ion exchange resin catalyst disposed therein;
circulating the resultant mixture collected in said first section through said second section whereby said n-dodecyl mercaptan and said formaldehyde catalytically react to form said dodecyl hydroxymethyl sulfide;
heating the contents of said reaction zone during said reaction to vaporize an azeotropic mixture by the water in said aqueous formaldehyde solution and said hexane solvent;
withdrawing said vaporized azeotropic mixture from said reaction zone during said reaction;
condensing said vaporized azeotropic mixture;
separating the condensed azeotropic mixture into condensed water and condensed hexane components;
withdrawing said condensed water component;
returning said condensed hexane component to said reaction zone;
withdrawing said dodecyl hydroxymethyl sulfide and said hexane solvent from said reaction zone; and
separating said dodecyl hydroxymethyl sulfide from said hexane solvent.

15. The process of claim 14 wherein said solid acid-type ion exchange resin catalyst is a strongly acidic macroreticular cation exchange resin.

16. The process of claim 15 wherein said mixture is heated to a temperature of about 100° C.

17. The process of claim 16 wherein said hexane solvent is separated from said dodecyl hydroxymethyl sulfide by vacuum evaporation of said hexane solvent.

* * * * *